United States Patent [19]

Fan

[11] Patent Number: 5,722,961
[45] Date of Patent: Mar. 3, 1998

[54] FLOW CONTROL DEVICE FOR USE WITH AN INTRAVENOUS SET

[75] Inventor: Cheng-Kuo Fan, Kaohsiung, Taiwan

[73] Assignee: King-He Hung, San Chung, Taiwan

[21] Appl. No.: 501,618

[22] Filed: Jul. 12, 1995

[51] Int. Cl.[6] .................................................. A61M 5/00
[52] U.S. Cl. ........................... 604/254; 604/90; 604/127; 604/256; 137/403; 137/433; 137/451
[58] Field of Search .................... 604/80, 89–91, 604/127, 131, 183, 245–7, 249, 251–2, 254–6, 320–1, 323; 222/66; 137/403, 433, 451

[56] References Cited

FOREIGN PATENT DOCUMENTS 0073613  6/1970  Germany ........................ 604/254

*Primary Examiner*—Michael Powell Buiz
*Assistant Examiner*—Bhisma Mehta
*Attorney, Agent, or Firm*—Bacon & Thomas

[57] ABSTRACT

Disclosed is a flow control device for use with an intravenous set to control the flow of medicinal fluid in a barrel into patient's body. The flow control device comprises a floating member capable of being supported for floating by the buoyancy of the medicinal fluid and having a first hollowed portion facing upwards so that the hollowed portion can contain medicinal fluid and a second hollowed portion facing downwards. A linkage bar is secured to the floating member by insertion into the second hollowed portion. A membranous member is coupled via the linkage bar to the floating member such that the membranous member moves along with the floating member. With the arrangement, as the barrel of the intravenous set is filled with a volume of medicinal fluid, the buoyancy of the medicinal fluid floats the floating member in such a way that the membranous member is brought away from the outlet of the intravenous set, thereby allowing the medicinal fluid to flow to the outlet; and as the medicinal fluid is gradually reduced in level, the floating member is lowered in level thereby and when the membranous member reaches at the bottom of the barrel, the membranous member blocks the outlet so as to stop the injection.

2 Claims, 3 Drawing Sheets

5,722,961

FLOW CONTROL DEVICE FOR USE WITH AN INTRAVENOUS SET

BACKGROUND OF THE INVENTION

1. Field of the Invention

The present invention relates to medical implements, and more particularly, to a flow control device for use with an intravenous set to control the flow of medicinal fluid injected into patients.

2. Description of Prior Art

FIG. 1 shows a prior art flow control device employed for use in an intravenous set. The prior art flow control device is disclosed in Malaysian Patent No. MY-104851-A to the same applicant. Other related references include U.S. Pat. Nos. 3,227,173; 4,055,176; and 4,640,306.

As shown in FIG. 1, the prior art flow control device includes a hollow member 2 in the barrel 1 for use as the flow control means. The hollow member 2 provides satisfactory effect in stopping the flow of medicinal fluid into the patient's body when there is only a small volume of medicinal fluid remaining in the barrel 1 so as to prevent air bubbles from entering into the patient's body.

There is, however, a drawback to the prior art flow control device that the hollow member 2 should be made with an appropriate weight which is difficult to determine. From experiments, it is found that if the hollow member 2 is weighty, it would benefit the downward pressure that allows it to tightly close the fluid outlet, but would otherwise too heavy to be fully supported by the buoyancy when the medicinal fluid is about to be used up. As a consequence, the hollow member 2 would drop to close the fluid outlet even when there is considered still a large enough volume of medicinal fluid that can be used for the injection. On the other hand, if the hollow member 2 is light, the downward pressure may not be enough to provide a tightly closed effect. Therefore, the determination of a suitable weight for the hollow member 2 is always a difficult problem for the manufacturer. Furthermore, there exists a need for a flow control device that can be manufactured separately and can be used with intravenous sets of various sizes.

SUMMARY OF THE INVENTION

It is therefore a primary objective of the present invention to provide a flow control device for use with an intravenous set that would eliminate the problem presented to the aforementioned prior art.

It is another objective of the present invention to provide a flow control device for use with an intravenous set that can be used in conjunction with intravenous sets of various sizes.

In accordance with the foregoing and other objectives of the present invention, there is provided with a novel flow control device for use with intravenous set. The flow control device comprises a floating member capable of being supported for floating by the buoyancy of the medicinal fluid and having a first hollowed portion facing upwards so that the hollowed portion can contain medicinal fluid and a second hollowed portion facing downwards. A linkage bar is secured to the floating member by insertion into the second hollowed portion. A membranous member is coupled via the linkage bar to the floating member such that the membranous member moves along with the floating member. With the arrangement, as the barrel of the intravenous set is filled with a volume of medicinal fluid, the buoyancy of the medicinal fluid floats the floating member in such a way that the membranous member is brought away from the outlet of the intravenous set, thereby allowing the medicinal fluid to flow to the outlet; and as the medicinal fluid is gradually reduced in level, the floating member is lowered in level thereby and when the membranous member reaches at the bottom of the barrel, the membranous member blocks the outlet so as to stop the injection. Furthermore, the floating member is a cylindrical body having four ribs formed at equal intervals on its circumferential periphery for balancing the floating member when floating in the medicinal fluid; and the membranous member is a circular piece made of flexible material. The diameter of the membranous member is larger than that of the transversal cross-section of the floating member but is slightly less than the maximum transversal distance measured from one rib to the opposite one.

In another embodiment of the flow control device, the combined structure of the floating member and the membranous member is accommodated in a casing having a hollowed inside. This allows the flow control device to be separately manufactured.

BRIEF DESCRIPTION OF DRAWINGS

The present invention can be more fully understood by reading the subsequent detailed description of the preferred embodiments thereof with references made to the accompanying drawings, wherein.

DETAILED DESCRIPTION OF PREFERRED EMBODIMENT

First Preferred Embodiment

Figure 1:
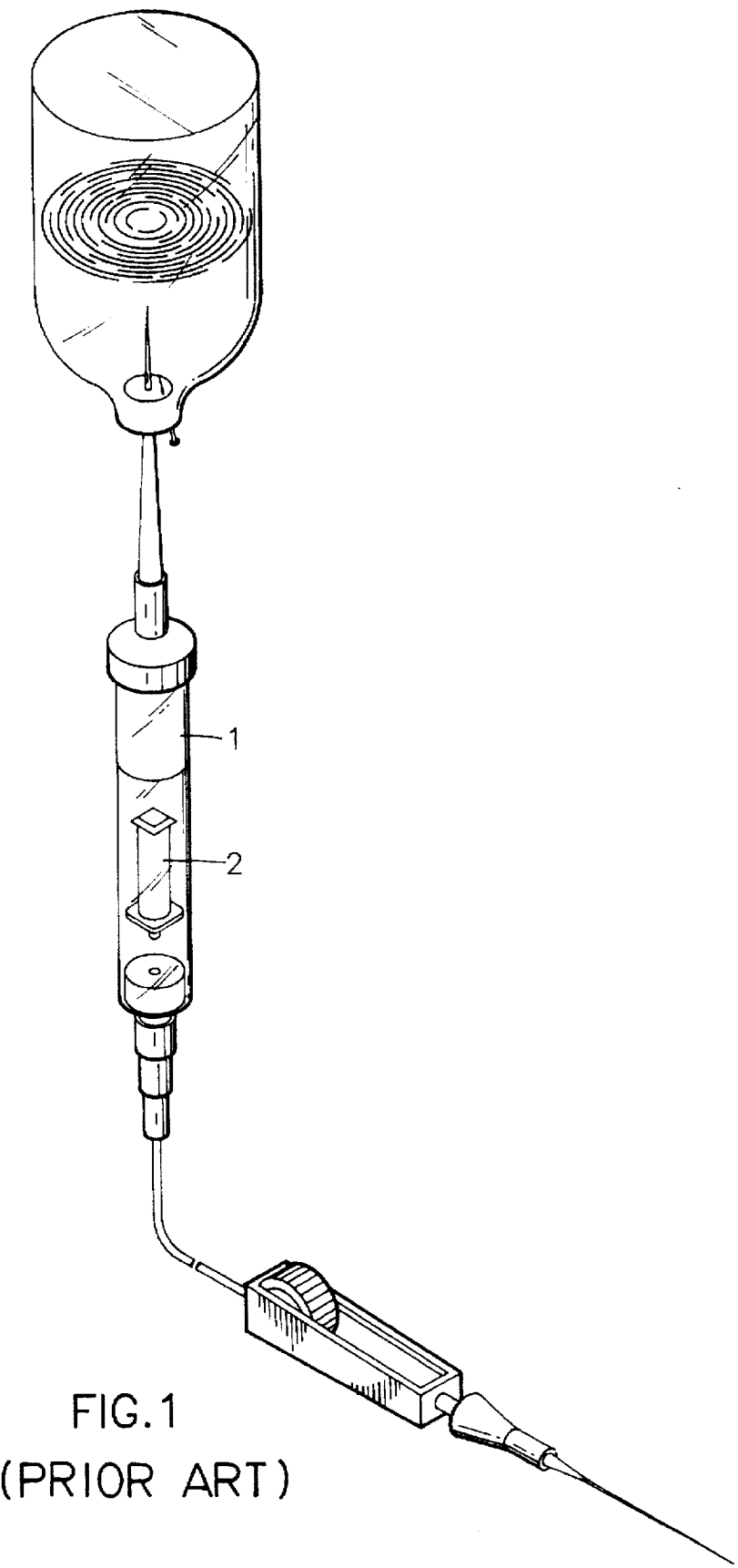
FIG. 1 shows a perspective view of an intravenous set employing a prior art flow control device.
Figure 2:
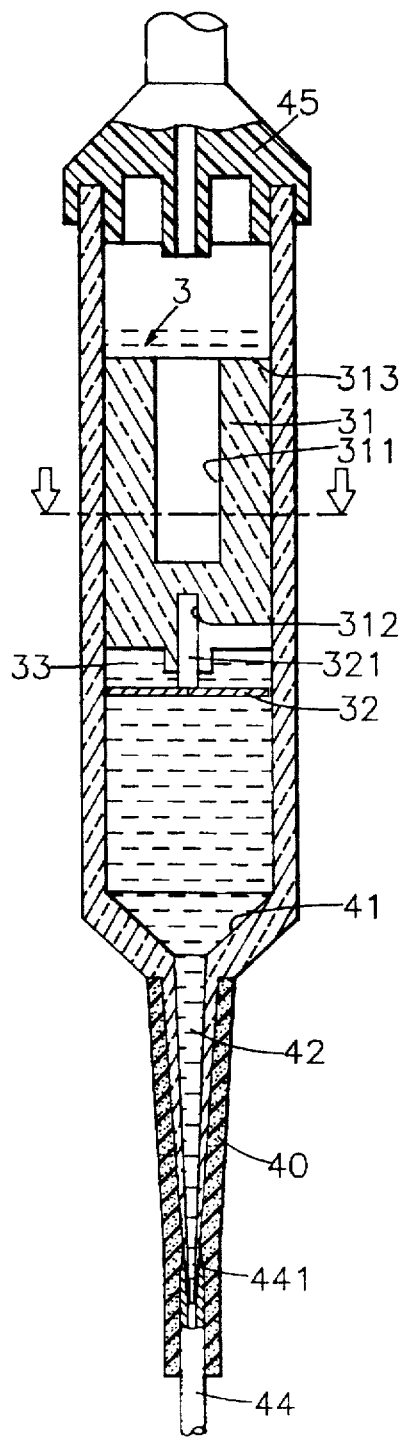
FIG. 2 shows a longitudinal cross-sectional view of an intravenous set employing a flow control device according to the first preferred embodiment of the present invention.

Referring to FIG. 2, there is shown an intravenous set employing a flow control device 3 according to the first preferred embodiment of the present invention. The intravenous set has a conventional structure that includes a barrel 4 for containing the medicinal fluid to be injected and an outlet tip 40 connected to the inlet 441 of a soft tube 44 connected to a needle cannula (not shown) used for insertion into the patient's body. A funnel-like portion 41 is formed at the bottom of the barrel 4 so as to channel the medicinal fluid into the outlet tip 40. During intravenous injection, the medicinal fluid in the barrel 4 flows through the passage 42 of the outlet tip 40 into the soft tube 44 so as to be subsequently injected into the patient's body.

The foregoing intravenous set employs the flow control device 3 according to the present invention for the flow control of the medicinal fluid. The flow control device 3 is accommodated in the barrel 4, and which is composed of a floating member 31 having a top hollowed portion 311 and a bottom hollowed portion 312. The top hollowed portion 311 is open toward the top and the bottom hollowed portion 312 is open toward the bottom and the two hollowed portions 311, 312 are not in connection. The bottom hollowed portion 312 is used to secure a linkage bar 321 used to couple the floating member 31 to a membranous member 32.

Figure 3:
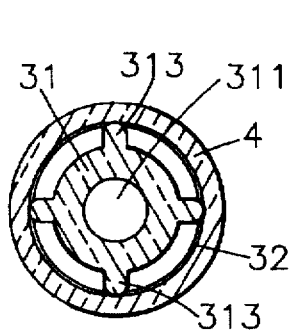
FIG. 3 shows a transversal cross-sectional view of the intravenous set of FIG. 2 cutting through the line III—III.

Referring also to FIG. 3, the floating member 31 includes four ribs 313 arranged at equal intervals around its circumferential periphery, each having its tip coming in touch with the inner wall of the barrel 4. These ribs 313 are used for balance purpose when the floating member 31 floats on the medicinal fluid. The membranous member 32 is a circular piece made of flexible material and which is coupled via the linkage bar 321 to the floating member 31. A gap 33 is formed between the membranous member 32 and the bottom end of the floating member 31. The diameter of the membranous member 32 is larger than that of the transversal cross-section of the floating member 31 but is slightly less than the distance between the tips of two opposite ribs 313. This allows smooth movement of the floating member 31 within the barrel 4.

In assembly, the flow control device 3 can be easily inserted into the barrel 4 of the intravenous set and then a cap 45 acting as the outlet of a bottle (not shown) containing the medicinal fluid is used to cover the top of the intravenous set. When the barrel 4 is filled with medicinal fluid, the floating member 31 can float on the medicinal fluid such that the membranous member 32 is kept away from the funnel-like portion 41 at the bottom of the barrel 4. The medicinal fluid in the barrel 4 thereby can flow into the passage 42 of the outlet tip 40 to be directed subsequently via the soft tube 44 into the patient's body.

Figure 4:
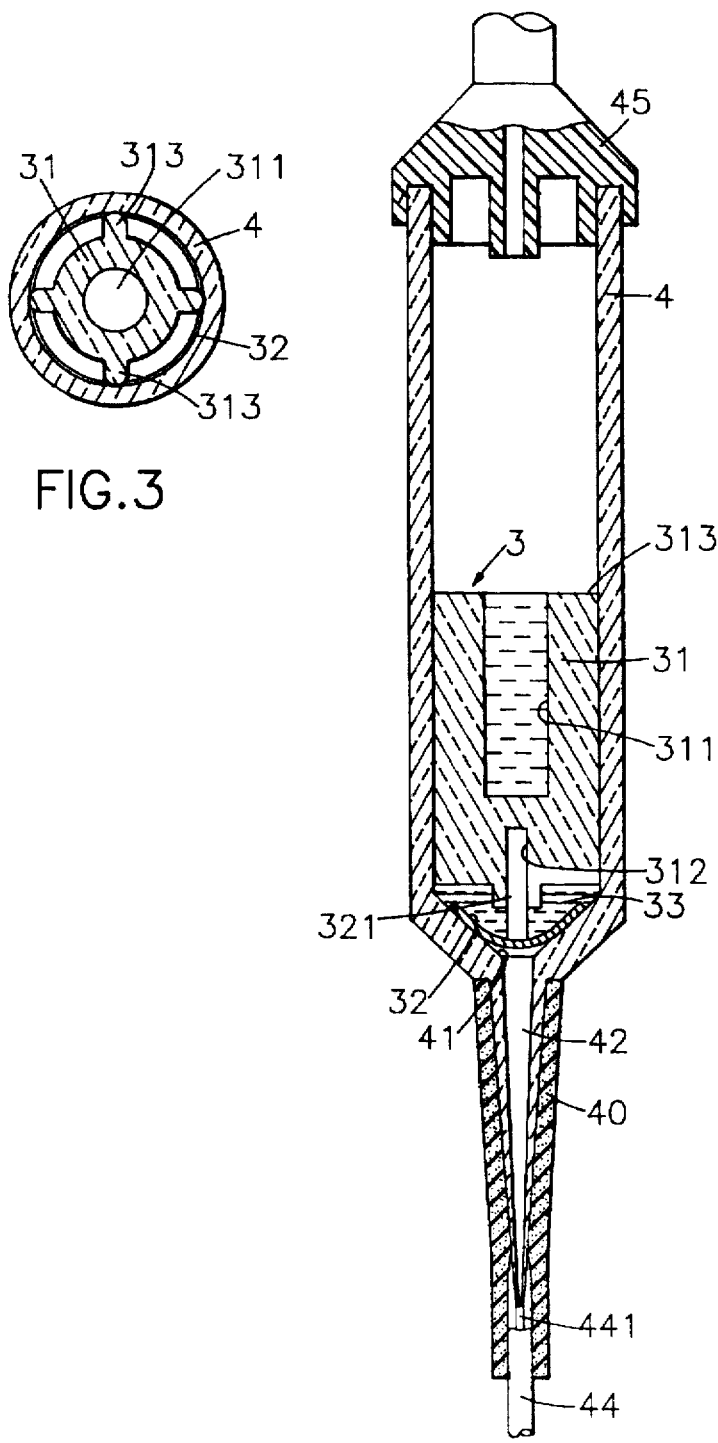
FIG. 4 shows the intravenous set of FIG. 2 in closed condition when a membranous member blocks the outlet of the medicinal fluid.

As time goes by, the medicinal fluid in the barrel 4 is gradually lowered in level and so the floating member 31 along with the membranous member 32. At the time the membranous member 32 reaches at the bottom (apex) of the funnel-like portion 41, as illustrated in FIG. 4, the membranous member 32 acts as a valve that closes the flow of the medicinal fluid into the passage 42 of the outlet tip 40. At this time, a small volume of medicinal fluid is still left above the membranous member 32, i.e., in the gap 33 between the membranous member 32 and the bottom of the floating member 31; and another volume of medicinal fluid is left in the top hollowed portion 311 of the floating member 31. The combined weight of the floating member 31 along with that of the two volumes of remaining medicinal fluid exerts a pressing force downwards against the membranous member 32 so that the closing by the membranous member 32 is tightly sealed.

To continue the injection, a new bottle of medicinal fluid (not shown) can be replaced. After that, the barrel 4 should be squeezed properly to reduce the pressure inside so that medicinal fluid from the new bottle can flow into the barrel 4. With the barrel 4 again filled with medicinal fluid, the flow control device 3, i.e., the floating member 31 along with the membranous member 32 will float in the medicinal fluid so that the membranous member 32 is brought away from the funnel-like portion 41, thereby allowing the medicinal fluid to flow into the passage 42 of the outlet tip 40. The injection of medicinal fluid into the patient's body thus can be continued.

Second Preferred Embodiment

Figure 5:
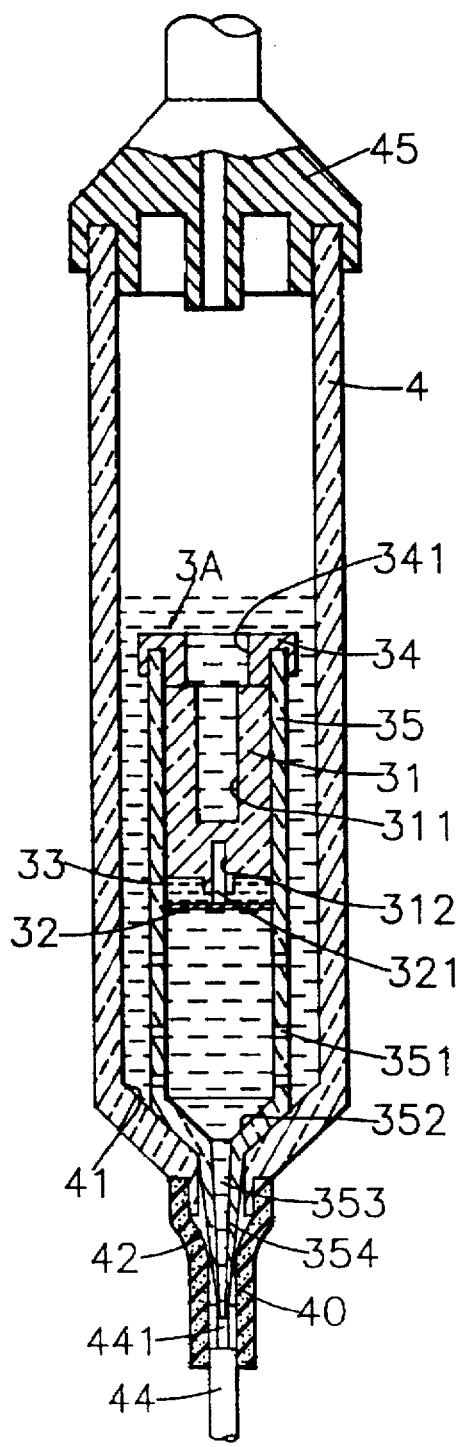
FIG. 5 shows a longitudinal cross-sectional view of an intravenous set employing a flow control device according to the second preferred embodiment of the present invention.

Referring to FIG. 5, there is shown an intravenous set employing a flow control device 3a according to the second preferred embodiment of the present invention. In this embodiment, the flow control device 3a uses a barrel-like casing 35 to house the floating member 31 and the membranous member 32. The flow control device 3a thus forms a separate unit that can be easily inserted into the barrel 4 of the intravenous set. The barrel-like casing 35 has its bottom end conically-shaped to form a funnel-like portion 352 coupled to a needle-like tip 354 having a fluid passage 353 therethrough. A plurality of holes 351 are formed on the wall of the barrel-like casing 35 so that the medicinal fluid outside the barrel-like casing 35 can flow into the inside. Further, a cap 34 having a through hole 341 and connected to the floating member 31 is mounted on the top of the barrel-like casing 35 so as to secure the floating member 31 in position.

To use the flow control device 3a in conjunction with the intravenous set, the nurse can simply insert the needle-like tip 354 at the bottom of the barrel-like casing 35 through the outlet opening of the barrel 4 into the inlet 441 of the soft tube 44. After that, a cap 45 acting as the outlet of a bottle (not shown) containing the medicinal fluid is used to cover the top of the intravenous set. The medicinal fluid from the bottle (not shown) thus can flow into the barrel 4 of the intravenous set through the inlet hole on the cap 45 and then fill the inside of the barrel-like casing 35 through the holes 351 and the hollowed portion 311 through the hole 341 on the cap 34. As the level of the medicinal fluid gets higher, the buoyancy of the medicinal fluid causes the flow control device 3a to rise such that the membranous member 32 is brought away from the funnel-like portion 352 where it blocks the entrance of the fluid into the fluid passage 353 in the needle-like tip 354. As a result, the medicinal fluid can flow from the inside of the barrel 4 through the holes 351 on the wall of the barrel-like casing 35 into the inside of the barrel-like casing 35, and then onwards through the fluid passage 353 in the needle-like tip 354 and the soft tube 44 into the patient's body.

Figure 6:
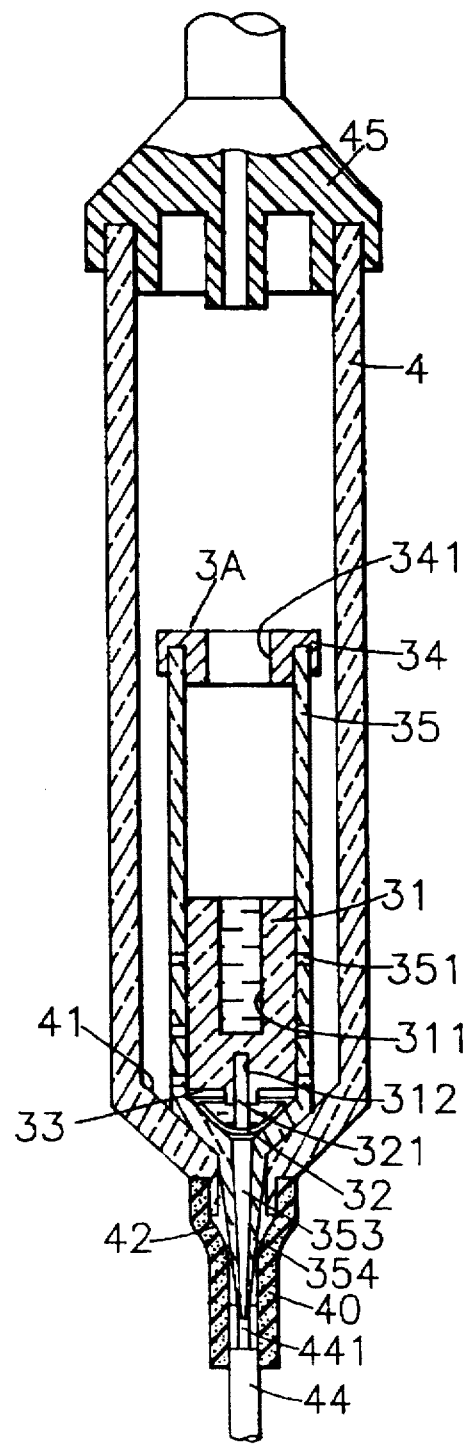
FIG. 6 shows the intravenous set of FIG. 5 in closed condition when the feeding of the medicinal fluid is stopped.

Similarly as in the first preferred embodiment, when the medicinal fluid is about to be used up, the level of the medicinal fluid lowers gradually such that the flow control device 3a supported by the buoyancy of the medicinal fluid also lowers gradually. At the time the membranous member 32 reaches at the funnel-like portion 352, as illustrated in FIG. 6, the membranous member 32 closes the entrance of the flow of the medicinal fluid into the fluid passage 353 in the needle-like tip 354.

The present invention has been described hitherto with exemplary preferred embodiments. However, it is to be understood that the scope of the present invention need not be limited to the disclosed preferred embodiments. On the contrary, it is intended to cover various modifications and similar arrangements within the scope defined in the following appended claims. The scope of the claims should be accorded the broadest interpretation so as to encompass all such modifications and similar arrangements.

What is claimed is:

1. A flow control device for use with an intravenous set having a barrel for containing medicinal fluid, the barrel having an outlet, the flow control device comprising:

(a) a generally cylindrical casing located in the barrel, the casing having a hollowed interior, a casing outlet opening in communication with the hollowed interior and the outlet of the barrel, an upper end and a wall having a plurality of holes so as to enable medicinal fluid in the barrel to enter the hollowed interior;

(b) a floating member located within the hollowed interior of said casing, supported for floating by the buoyancy of the medicinal fluid, and having an upper surface, a lower surface, a peripheral surface, and a hollowed portion opening through the upper surface so that the hollowed portion contains medicinal fluid;

(c) a valve including a linkage bar secured to said floating member and located in the casing, the valve including a membranous member having a circular configuration and made of flexible material coupled via said linkage bar to said floating member such that said membranous member is spaced from the bottom surface of the floating member and moves with said floating member such that the membranous member is below a surface of the medicinal fluid in the barrel when the floating member is floating in the medicinal fluid; and wherein as the barrel of the intravenous set is filled with medicinal fluid, the buoyancy of the medicinal fluid floats said floating member in the casing such that said membranous member is brought away from the outlet opening of the casing, thereby allowing the medicinal fluid to flow to the outlet of the barrel; and wherein as the volume of medicinal fluid in the barrel is gradually reduced in level, said floating member is lowered and when said membranous member reaches a bottom of the casing, the weight of the medicinal fluid in the hollowed portion and the medicinal fluid above the membranous member causes said membranous member to block the outlet of the casing so as to stop the injection.

2. A flow control device as claimed in claim 1, wherein said floating member comprises a generally cylindrical body having four ribs extending outwardly at equal intervals on its circumferential periphery for balancing said floating member when floating in the medicinal fluid.

* * * * *